(12) United States Patent
Takaoka et al.

(10) Patent No.: US 6,703,626 B2
(45) Date of Patent: Mar. 9, 2004

(54) MASK DEFECT REPAIR METHOD

(75) Inventors: Osamu Takaoka, Chiba (JP); Satoru Yabe, Chiba (JP)

(73) Assignee: Seiko Instruments Inc., Chiba (JP)

(*) Notice: Subject to any disclaimer, the term of this patent is extended or adjusted under 35 U.S.C. 154(b) by 0 days.

(21) Appl. No.: 10/047,974

(22) Filed: Jan. 15, 2002

(65) Prior Publication Data

US 2002/0096635 A1 Jul. 25, 2002

(30) Foreign Application Priority Data

Jan. 16, 2001 (JP) ...................................... 2001-007370

(51) Int. Cl.[7] .............................................. G01N 23/00
(52) U.S. Cl. ........................... 250/492.21; 250/492.21; 250/306; 250/423 F; 250/307; 216/66; 216/63; 430/5; 430/322; 430/30
(58) Field of Search ............................. 250/492.21, 306, 250/423 F, 307; 216/66, 63; 430/5, 322, 30

(56) References Cited

U.S. PATENT DOCUMENTS 6,322,935 B1 * 11/2001 Smith ............................ 430/5
6,392,229 B1 * 5/2002 Dana et al. .................. 250/306

OTHER PUBLICATIONS

Dana et al. "AFM–Based Lithography Metrology Tool", Pub. No. US 2002/0158197 A1, publication date:: Oct. 31, 2002.*

* cited by examiner

Primary Examiner—John R. Lee
Assistant Examiner—Zia R. Hashmi
(74) Attorney, Agent, or Firm—Adams & Wilks

(57) ABSTRACT

First, a region including the defect is observed with the atomic force microscope (AFM) and a pattern putting together the shape and position of the defect is extracted from and AFM image. The extracted pattern is then converted to a shape format for a for an ion beam defect repairing apparatus and transferred. At this time, a pattern that is observable with the ion beam defect repairing apparatus is selected as a position alignment pattern. The extracted/converted position alignment pattern is combined with a pattern corresponding to a secondary electron image or a secondary ion image. Repairing of the irradiation region and similar repairing is then performed with respect to matching processing for a pattern for a normal secondary ion image or secondary electron image for the ion beam defect repairing apparatus and extraction is performed by the AFM. A defect region finely adjusted using alignment of the position alignment pattern is then corrected using an ion beam.

11 Claims, 4 Drawing Sheets

MASK DEFECT REPAIR METHOD

BACKGROUND OF THE INVENTION

The present invention relates to a method for correcting defects in a photomask or reticule. Photomasks of the related art are typically formed using opaque metal films such as Cr or an attenuated phase shifting mask material such as MoSiON deposited by sputtering onto a glass substrate such as silicon glass so that the mask pattern brings about a transformation due to differences in the transmittance of light. Therefore, when performing monitoring/repair using a defect repairing apparatus employing an ion beam as a charged particle beam, electrons are irradiated to perform charge neutralization in order to prevent primary ions from being curved due to charge-up of the mask and in order to prevent it from becoming possible to no longer observe secondary ion images or secondary electron images. When design rules are not severe, image used for confirmation of defective regions that are sufficient for practical purposes can be obtained by optimizing the charge neutralization conditions. However, as a result of recent severity of design rules, with isolation patterns or patterns (OPC patterns) introduced to correct optical proximity effects of exposure apparatus, it has become difficult to observe shapes correctly at the ends of patterns, and charge neutralization conditions have become different for every pattern. In addition, the presence of small features has meant that viewing has become impossible even if charge neutralization is performed using electrons. Necessary repair to satisfy the specifications sought in defect repair cannot be achieved because correct confirmation of defects cannot be achieved for these kind of detailed isolation patterns or OPC patterns.

SUMMARY OF THE INVENTION

In addition to having a high spatial resolution, an atomic force microscope is also capable of observing insulators with a high resolution. First, a region of a mask including a defect is observed with the atomic force microscope (AFM) and a pattern including the shape and position of the defect is extracted from an AFM image. The extracted pattern is then converted to a shape format usable by a repairing apparatus using an ion beam and saved. Then a pattern that is observable with the repairing apparatus employing an ion beam is selected as a position alignment pattern. The mask in which the defect is recognized using the AFM is then moved to the apparatus employing an ion beam. A pattern including the defect extracted and converted from the AFM image is then read in. A position alignment pattern for an extracted pattern is then combined with a pattern corresponding to a secondary electron image for the repairing apparatus employing an ion beam and extraction is performed by the AFM. A defect region finely adjusted using alignment of the position alignment pattern is then corrected using an ion beam.

Operation

An AFM capable of high resolution observation even for insulating materials is used to recognize defects and a pattern that is not subject to the influence of charging up is lined up for position alignment. High precision repairing of defects which it was, up until now, difficult to correct using defect repairing apparatus employing ion beams is now possible. Further, if the extent of irradiation with an ion beam is controlled by actively utilizing height information obtained during AFM observation, a problem of detecting end points using ion signals for which images could not be seen due to charging up is resolved, and high quality repairing of defects is possible even for black defects.

Figure 1:
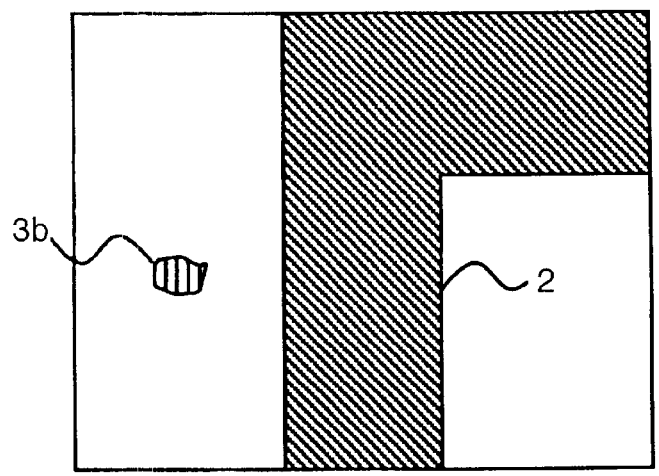
FIG. 1 is a view showing a pattern for providing position alignment with a defect region when observing with an AFM.

DESCRIPTION OF THE NUMERALS 1 defect region recognized by AFM observation
2 pattern for position alignment observed by AFM
3a defect region converted to shape format for ion beam defect repairing apparatus
3b defect region subjected to pattern superimposition and irradiation region correction
4 position alignment pattern converted to shape format for ion beam defect repairing apparatus
5 defect region observed by ion beam defect repairing apparatus
6 position alignment pattern observed by an ion beam defect repairing apparatus
7 glass substrate
8 ion beam
9 gas injector
10 source gas for clear defect repairing film
11 clear defect repairing film

DETAILED DESCRIPTION OF THE INVENTION

The following is a description of the present invention applied to the case where shapes of opaque defects cannot be correctly recognized due to charging up.

A stage is moved to a location where a defect is found using the defect inspection tool and a region including the defect is observed using an atomic force microscope (AFM).

Figure 2:
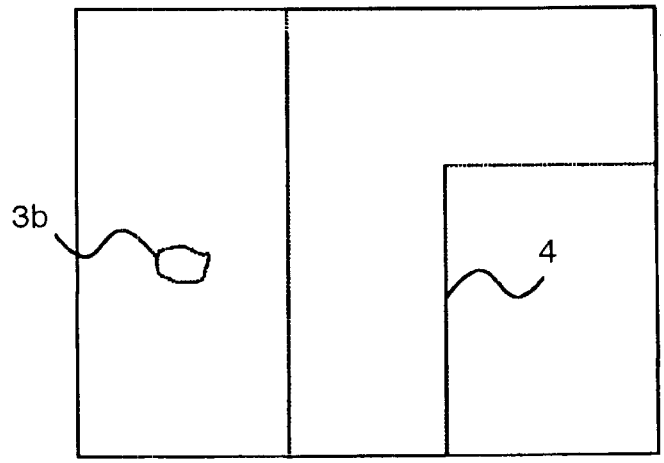
FIG. 2 is a view showing a pattern for providing position alignment with a defect region extracted using an AFM converted to a shape format for use with an ion beam defect repairing apparatus.

A pattern 2 for performing position alignment for a region 1 including a defect from an AFM image shown in FIG. 1 is extracted as shown in FIG. 2. The extracted pattern is then converted to a repairing apparatus-specific shape format using an ion beam and this is saved. At this time, a pattern that is not influenced by charge-up even with a repairing apparatus employing an ion beam is selected as a position alignment pattern 2. Data for a defect region 3a extracted/converted from the AFM image and a position alignment pattern 4 is transferred to the repairing apparatus employing an ion beam.

Figure 3:
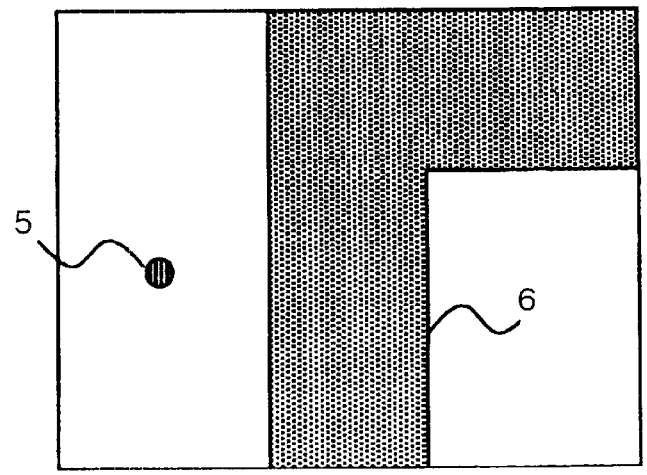
FIG. 3 is a view showing a pattern for providing position alignment with a defect region when observing with an ion beam defect repairing apparatus.
Figure 4:
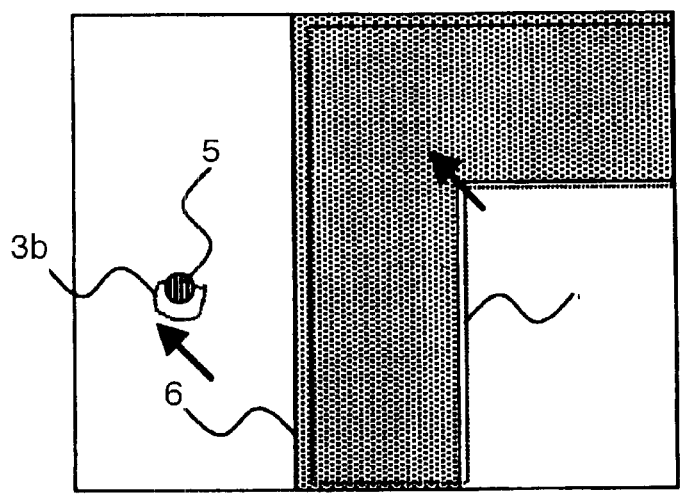
FIG. 4 is a view illustrating combination with a pattern for position alignment observed by an ion beam defect repairing apparatus for a pattern for position alignment extracted by an AFM.
Figure 5:
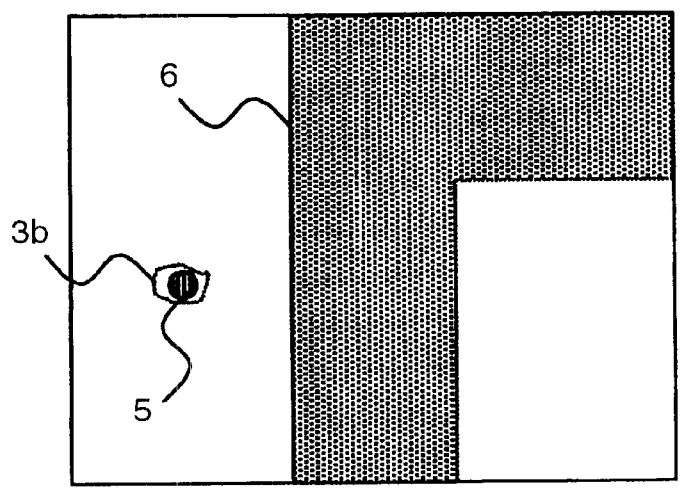
FIG. 5 is a view showing a region actually processed by an ion beam after combining the patterns.
Figure 6:
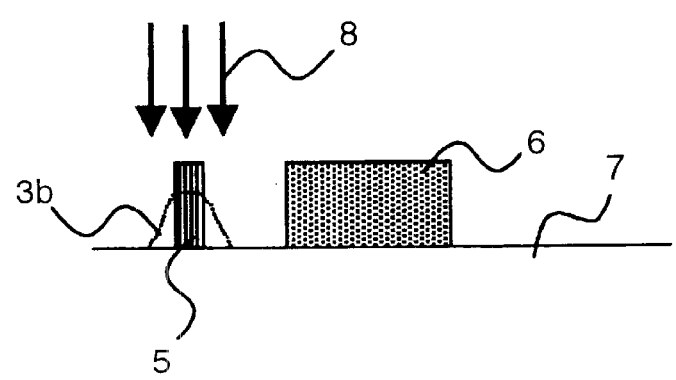
FIG. 6 is an outline cross-sectional view showing processing using an ion beam in combination for a defect region recognized using an AFM that effectively exhibits the feature of the present invention.

A mask for which a defect region has been recognized using an AFM is then moved to the apparatus employing the ion beam and the stage is moved to the location where the defect was found using the defect scanning apparatus. A secondary electron image or secondary ion image for the region including the defect is then observed using the repairing apparatus employing the ion beam. A position alignment pattern 4 extracted from the AFM image is then lined up with a pattern corresponding to a secondary electron image or secondary ion image 6 for a region including the defect shown in FIG. 3 as shown in FIG. 4. After the kind of pattern adjustment shown in FIG. 5 is complete, irradiation region repairing and similar repairing is performed taking into consideration the shape of an ion beam with respect to mapping processing for patterns from normal secondary ion images or secondary electron images for the repairing apparatus employing an ion beam. Rather than the defect region 5 that can be seen in a secondary ion image or secondary electron image, the defect region 3a extracted by the AFM and the defect region 3b subjected to the aforementioned lining up and correction are used in removal/repair using the ion beam as shown in FIG. 6.

End point detection utilizing ion signals and a contrast disparities due to materials for secondary electrons is not successful because an image cannot be seen because of charging up. Height information for the defect region at the time of defect recognition by the AFM as shown in FIG. 6 is also collected. The extent of irradiation with an ion beam during opaque defect repairing by the defect repairing apparatus using an ion beam based on this information is then decided upon, and it is ensured that there is little material left after removal and little damage to a glass substrate 7.

Next, a description is given of an example of the present invention applied to the case where a opaque defect cannot be seen with an ion beam defect repairing apparatus because of charging up.

Figure 7:
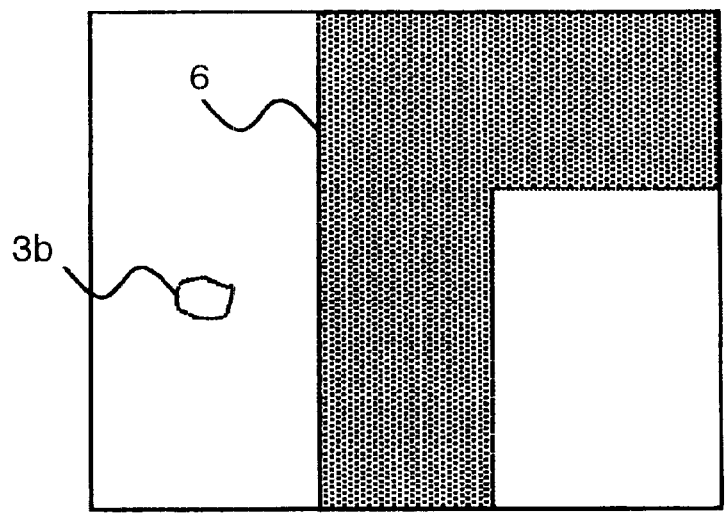
FIG. 7 is a view showing a region actually processed with an ion beam after combining patterns for the case where defects cannot be seen using an ion beam defect repairing apparatus.
Figure 8:
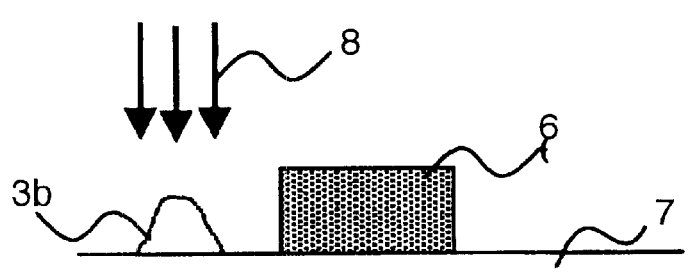
FIG. 8 is an outline cross-sectional view showing a region processed with an ion beam when opaque defects cannot be seen using an ion beam defect repairing apparatus.

A pattern for position alignment with the defect region is extracted from an AFM image using the same method as for the case for where defect shape could not be correctly recognized because of charge up and converted data is then transferred to repairing apparatus employing an ion beam. Secondary electron image or secondary ion image observation of a region including the defect is then carried out by the repairing apparatus employing the ion beam. The position alignment pattern 4 extracted by the AFM as shown in FIG. 7 is then lined up with the position alignment pattern 6 obtained for the secondary ion image or secondary electron image. The defect cannot be seen for the secondary ion image or the secondary electron image but the ion beam is irradiated as shown in FIG. 8 onto the region 3b extracted by the AFM and subjected to positional alignment and irradiation position repairing, and the opaque defect is repaired.

Figure 9:
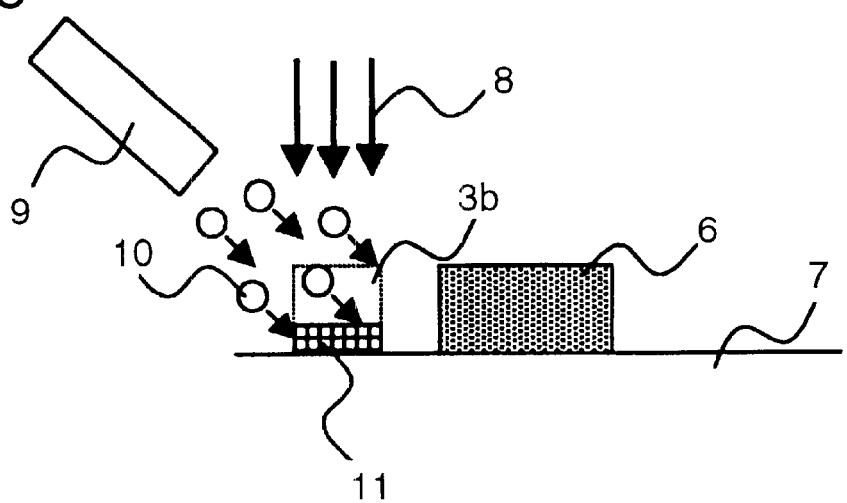
FIG. 9 is an outline cross-sectional view illustrating the case where clear defects are repaired using the present invention.

The above description is given for opaque defects. However, if a region 3a extracted by an AFM and subjected to position alignment and irradiation position correction is irradiated with an ion beam while supplying a clear defect repairing film source gas 10 from a gas injector 9 located in the vicinity of a mask as shown in FIG. 9, a clear defect repairing film 11 is deposited and the clear defect can be repaired using the same procedure as for the black defect.

Figure 10:
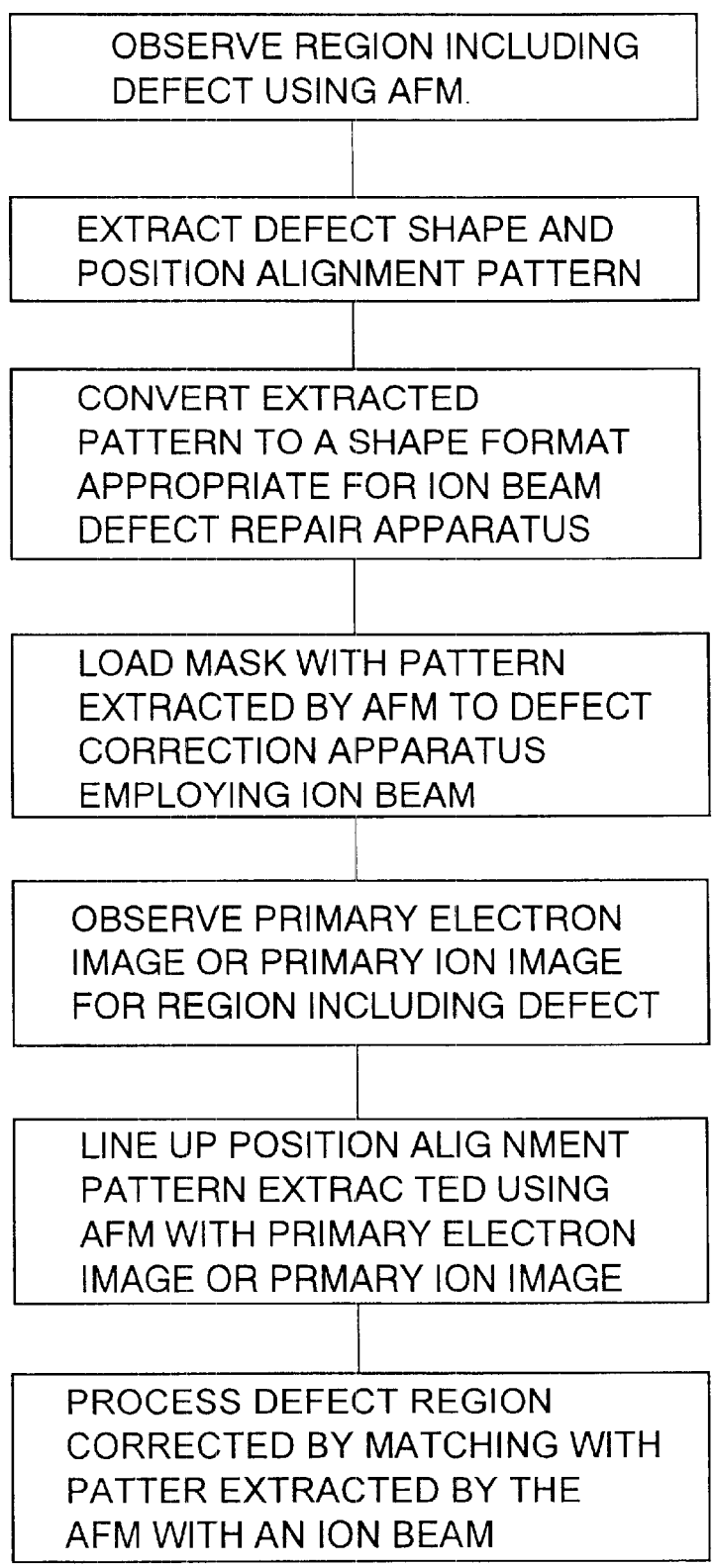
FIG. 10 is a flowchart showing a defect repairing procedure of the present invention.

The flow for the defect repairing of the present invention is shown in FIG. 10.

As described above, according to this invention, an AFM that is capable of recognizing defects that easily become charged up and is capable of high resolution observation for defect recognition even with insulating materials such as masks is used. The precise shape and position of defects can therefore be understood, and processing is performed in combination with a pattern used for position alignment during defect repairing using an ion beam that is not influenced by charging up. Defects that up to now were subject to the influence of charging up which made the use of defect repairing apparatus employing ion beams difficult can therefore now be repaired in a highly accuracy manner and with a high degree of quality.

What is claimed is:

1. A method for correcting a binary mask or an OPC-pattern, comprising: a step of extracting a pattern for position alignment including a defect region of the mask from a high-resolution image of a region including the defect region obtained using an atomic force microscope when the image of the defect region could not accurately be obtained using a mask defect repairing apparatus employing an ion beam due to charge-up of the defect region by the ion beam; a step of converting the pattern for position alignment including the defect region into a shape format usable by the mask defect repairing apparatus; a step of aligning the mask defect repairing apparatus by combining the extracted position alignment pattern in the shape format with a position alignment pattern comprised of a secondary charged particle image of a region of the mask including the defect region obtained using the ion beam produced by the mask defect repairing apparatus; and a step of repairing the extracted defect region in the shape format using the ion beam produced by the mask defect repairing apparatus.

2. A method for correcting a mask according to claim 1; wherein the step of repairing the defect using the ion beam is performed in combination with a secondary charged particle image of the defect.

3. A method for correcting a mask according to claim 1; wherein the defect is an opaque defect.

4. A method for correcting a mask according to claim 3; wherein the step of repairing the defect using the ion beam is performed in combination with a secondary charged particle image of the defect.

5. A method for correcting a mask according to claim 1; wherein the defect is a transparent defect.

6. A method for correcting a defect in a mask, comprising the steps of:

observing a region of the mask including the defect using an atomic force microscope;

extracting a position alignment pattern including the defect shape and a surrounding region of the mask from the image obtained by the atomic force microscope;

converting the extracted position alignment pattern including the defect into a graphic format pattern usable by an ion beam defect repairing apparatus;

providing the converted position alignment pattern to the ion beam defect repairing apparatus;

obtaining a secondary charged particle image of a region of the mask not subject to charge-up;

aligning the ion beam defect repairing apparatus by combining the graphic format pattern with the secondary charged particle image; and repairing the defect area in the graphic format using the ion beam.

7. A method for repairing a defect in a mask using a focused ion beam apparatus, comprising the steps of:

obtaining a first image of a sample including the defect with a high-resolution microscope;

converting the first image into a form readable by an ion beam defect repairing apparatus;

obtaining a second image of the sample comprised of a secondary ion image or a secondary electron image with the ion beam defect repairing apparatus;

combining the converted first image and the second image to align a focused ion beam produced by the ion beam defect repairing apparatus; and repairing the defect using the focused ion beam.

8. A method of repairing a defect in a mask according to claim 7; wherein the high-resolution microscope comprises an atomic force microscope.

9. A method of repairing a defect in a mask according to claim 7; wherein the atomic force microscope is capable of observing insulating materials.

10. A method of repairing a defect in a mask according to claim 7; wherein the defect is an opaque defect.

11. A method of repairing a defect in a mask according to claim 7; wherein the defect is a transparent defect.

* * * * *